United States Patent [19]

Villa et al.

[11] Patent Number: 5,268,491
[45] Date of Patent: Dec. 7, 1993

[54] PROCESS FOR THE DEHALOGENATION OF NAPHTHALENE DERIVATIVES

[75] Inventors: Marco Villa; Paolo Cavalleri, both of Milan, Italy

[73] Assignee: Zambon Group S.p.A., Vicenza, Italy

[21] Appl. No.: 962,518

[22] Filed: Oct. 16, 1992

[30] Foreign Application Priority Data

Oct. 18, 1991 [IT] Italy .................. MI91A002767

[51] Int. Cl.$^5$ .................. C07D 317/12; C07D 317/32; C07C 41/24; C07C 41/22
[52] U.S. Cl. .................. 549/453; 549/347; 549/374; 549/450; 549/452; 549/451; 568/592
[58] Field of Search .................. 568/592; 549/347, 374, 549/450, 453, 452, 451

[56] References Cited

FOREIGN PATENT DOCUMENTS

| | | |
|---|---|---|
| 0035305 | 9/1981 | European Pat. Off. . |
| 0048136 | 3/1982 | European Pat. Off. . |
| 0064394 | 11/1982 | European Pat. Off. . |
| 0081993 | 6/1983 | European Pat. Off. . |
| 0101124 | 2/1984 | European Pat. Off. . |
| 0034871 | 7/1985 | European Pat. Off. . |
| 0163338 | 12/1985 | European Pat. Off. . |
| 0203557 | 12/1986 | European Pat. Off. . |
| 0158913 | 7/1988 | European Pat. Off. . |

OTHER PUBLICATIONS

Manabu Nobe, et al., Journal of Organic Chemistry "Hard Acid and Soft Nucleophile Systems. 8.$^1$ Reductive Dehalogenation of O-And P-Halophenols and Their Derivatives" vol. 49, No. 19, 1984, pp. 3641-3643.
*The Hydrogenolysis of Organic Halides,* A. R. Pinder, Georg Thieme Verlag—Stuttgart—New York, (1980) pp. 425-452.

*Primary Examiner*—Marianne M. Cintins
*Assistant Examiner*—Margaret J. Page
*Attorney, Agent, or Firm*—Oblon, Spivak, McClelland, Maier & Neustadt

[57] ABSTRACT

A process for the selective dehalogenation in position 5 of the naphthalenic nucleus of compounds of formula

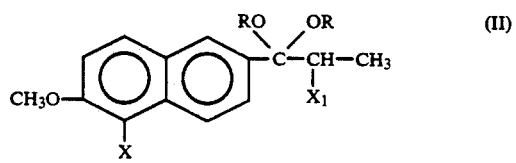

(II)

(wherein X, X$_1$ and R have the meanings reported in the description) by treatment with a dehalogenating agent selected among hydrogen sulfide, aliphatic thiols or mixtures thereof in an inert anhydrous solvent at acid pH.

7 Claims, No Drawings

PROCESS FOR THE DEHALOGENATION OF NAPHTHALENE DERIVATIVES

The present invention relates to a process for the dehalogenation of haloaromatic substrates and more in particular it relates to a process for the selective dehalogenation of halogenated naphthalene derivatives.

The technique of selective removal of a halogen atom from the aromatic nucleus is illustrated in particular for its use on intermediates in the synthesis of 2-(6-methoxy-2-naphthyl)propionic acid [whose S(+)isomer, known as Naproxen, is an antiinflammatory drug] since this specific application presents a remarkable practical importance.

Numerous processes for the synthesis of Naproxen comprise the preparation of a α-halo-ketal of (6-methoxy-2-naphthyl)-ethyl-ketone. In some of these processes the α-halo-ketal is prepared by halogenation of (6-methoxy-2-naphthyl)-ethyl-ketone or of a ketal thereof. As an example we report the European Patents No. 34871 (Blaschim), No. 35305 (Blaschim), No. 48136 (Sagami), No. 64394 (Syntex), No. 81993 (Syntex), No. 101124 (Zambon) and No. 158913 (Zambon).

In the process described in European Patent No. 158913 the introduction of the halogen atom in α-position is diastereoselective and leads to a mixture in which a diastereoisomer strongly prevails.

The halogenating agent commonly used is bromine since it is less expensive, more easily handy and available.

Nevertheless, the main drawback connected with the use of bromine consists in that it leads to the bromination in position 5 of the naphthalenic nucleus.

In other processes the α-halo-ketal is alternatively prepared by employing a halogenated naphthalene derivative as starting substrate.

For example in European Patent No. 163338 (Blaschim) a process for the preparation of Naproxen is described which starts from 1-chloro-2-methoxy-naphthalene thus obtaining α-halo-ketals of (5-chloro-6-methoxy-2-naphthyl)-ethyl-ketone.

Therefore in these processes becomes necessary to remove the halogen atom on the naphthalenic nucleus from one of the intermediates or from 2-(5-halo-6-methoxy-2-naphthyl)-propionic acid.

Independently of the preparation process used, the halogenation of the ketals of (6-methoxy-2-naphthyl)-ethyl-ketone (hereinafter indicated more briefly as compounds of formula I) is generally carried out in an anhydrous aprotic solvent.

Numerous reactives suitable for the dehalogenation of haloaromatic substrates [A. R. Pinder, Synthesis, 425, (1980)] and various methods for the dehalogenation of 2-(5-halo-6-methoxy-2-naphthyl)-propionic acid (Belgian Patent No. 892689—Alfa Chemicals) are known in the literature.

However these methods generally describe the possibility of employing aqueous protic solvents and therefore they cannot be applied on ketals since these are generally unstable in a protic solvent.

Furthermore some reactives such as hydrazine and metallic hydrides are dangerous and the use thereof is not advisable from an industrial point of view. Therefore, in the processes for the synthesis of Naproxen is in general necessary to carry out the dehalogenation from the most advanced intermediates which do not have the ketalic function, generally from 2-(5-halo-6-methoxy-2-naphthyl)-propionic acid or from esters thereof.

It appears clear to the man skilled in the art the economical advantage resulting from the possibility of carrying out the dehalogenation on an upstream intermediate of the synthesis and furthermore in the same environment of the halogenation reaction and in particularly mild conditions so as not to lead to epimerizations.

European patent No. 203557 (Zambon) describes a method of debromuration of α-bromo-ketals of (5-bromo-6-methoxy-2-naphthyl)-ethyl-ketone in the presence of an acid and of an aromatic compound such as phenols, phenolic ethers, arylketones and arylalkylketones as bromine acceptor.

We have now surprisingly found and it is object of the present invention a process for the selective dehalogenation in position 5 of the naphthalenic nucleus of compounds of formula

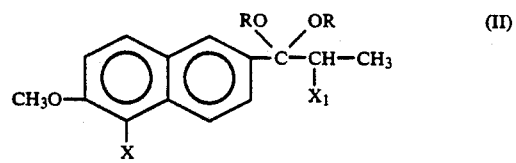

wherein X and $X_1$, the same or different, represent a bromine or chlorine atom; the two R radicals independently represent an alkyl, phenyl or benzyl; otherwise the two R radicals together represent $C_2$-$C_5$ alkylene that forms, together with the two oxygen atoms and the carbon to which they are bonded, a cyclic structure optionally alkyl-substituted; otherwise again they represent together a group

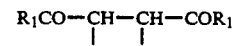

wherein the two $R_1$ radicals, the same or different, represent hydroxy, alkoxy or an aminic group, that comprises treating a compound of formula II with a dehalogenating agent selected among hydrogen sulfide, aliphatic thiols or mixtures thereof in an inert anhydrous solvent at acid pH.

The compounds of formula II present at least one asymmetric center on the aliphatic carbon atom to which the halogen atom is linked; the process according to the present invention can be indifferently applied both to the stereoisomeric mixtures and to the single stereoisomers.

Specific examples of dehalogenating agents are, beyond hydrogen sulfide, aliphatic thiols such as methylmercaptan, t.butylmercaptan, thioglycolic acid, 1,2-ethandithiol and mixtures thereof.

Exclusively for practical reasons it is preferred to employ t.butylmercaptan.

A further object of the present invention is the use of the dehalogenation reaction on compounds of formula II without isolating them, directly in the same reaction system in which they are formed by halogenation of compounds I, for example by bromination with bromine.

A practical way of carrying out the present invention is reported in the following scheme and hereinafter commented.

Scheme 1

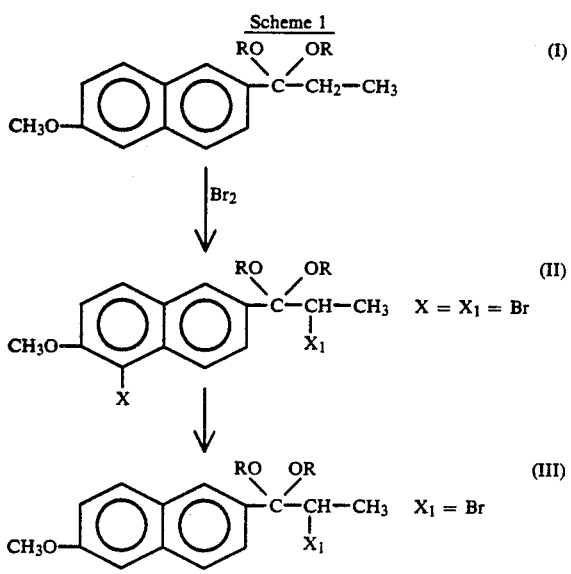

(R has the meanings above reported).

A compound of formula I is brominated, preferably with bromine, in an organic solvent such as benzene, toluene, nitrobenzene, chlorinated solvents and mixtures thereof.

Preferred solvents are methylene chloride and toluene.

Subsequently the dehalogenating agent is added to the reaction mixture, preferably t. butylmercaptan, operating at temperatures comprised between $-20°$ C. and $+20°$ C.

The dehalogenation reaction is carried out at acid pH; when it is carried out in the same reaction system of the bromination reaction the acidity already present, due to the production of HBr, is sufficient.

In alternative, mineral acids such as halogenhydric acids, organic acids such as trifluoroacetic acid or methanesulphonic acid, Lewis acids such as $ZnCl_2$ and $ZnBr_2$ or mixtures thereof, can be added, even in catalytic amounts.

The dehalogenating agent is employed in amounts comprised between 1 and 3 moles per mole of substrate, preferably about 2 moles.

Furthermore it is preferred to work at temperatures comprised between $-10°$ C. and $+10°$ C.

In a short time the reaction is finished and the ketal dehalogenated in position 5 of the naphthalenic nucleus can be isolated with very good yields and high purity or in alternative it can be employed just as it is, no need to isolate it, in the subsequent reactions.

The process object of the present invention presents remarkable practical advantages with respect to the other known processes for the synthesis of Naproxen which comprise the dehalogenation, such as the simplicity of operations, the selectivity of the dehalogenation in position 5 of the naphthalenic nucleus, the safety of the process that does not require the use of hydrogen or other dangerous substances such as hydrazine and metallic hydrides, the possibility of carrying out the dehalogenation on a less expensive intermediate (ketal).

Another important aspect is represented by the cheapness of the dehalogenating agents which are reagents of normal industrial use, easily available at low cost.

A further advantage is the possibility of applying the process object of the present invention even to the optically active compounds of formula II without having racemization or partial epimerization.

In order to better illustrate the present invention without however limiting it, the following examples are now given.

EXAMPLE 1

Bromine (47 g; 0.294 moles) was added in 45 minutes to a suspension of 2-ethyl-2-(6-methoxy-2-naphthyl)-4(R),5(R)-dimethoxycarbonyl-1,3-dioxolane (50 g; 0.134 moles) in toluene (150 ml) cooled to $-10°$ C. The mixture was kept under stirring at $-10°$ C. for 2 hours, then n.butylmercaptan (0.5 g; 5.5 mmoles) and by bubbling hydrogen sulfide (13.6 g; 0.401 moles) were added in 1 hour.

After 12 hours at $-10°$ C. the reaction mixture was poured into an aqueous solution of 8% sodium bicarbonate (100 ml). After separation of the phases, the organic phase was evaporated to residue under vacuum. A crude product (69.6 g) was obtained containing a mixture (55.7 g) of 2-[1(S)-bromoethyl]-2-(6-methoxy-2-naphthyl)-4(R),5(R)-dimethoxycarbonyl-1,3-dioxolane and its epimer having RRR configuration in a ratio 89.9:10.1 (yield 91.6%).

EXAMPLE 2

Bromine (5.3 g; 0.033 moles) was added in 30 minutes to a suspension of 2-ethyl-2-(6-methoxy-2-naphthyl)-4(R),5(R)-dimethoxycarbonyl-1,3-dioxolane (5.6 g; 0.015 moles) in toluene (12.6 ml) cooled to $-10°$ C. Then t.butylmercaptan (2.8 g; 0.031 moles) was added to the mixture which was kept under stirring at $-10°$ C. for 2 hours.

After 4 hours at $-10°$ C. the reaction mixture was poured into water (20 ml); after separation of the phases, the organic phase was washed with an aqueous solution of 10% sodium carbonate (10 ml) and evaporated to residue under vacuum. A crude product (9.3 g) was obtained containing a mixture (6.5 g) of 2-[1(S)-bromoethyl]-2-(6-methoxy-2-naphthyl)-4(R),5(R)-dimethoxycarbonyl-1,3-dioxolane and its epimer having RRR configuration in a ratio 90.7:9.3 (yield 95.6%).

EXAMPLE 3

Bromine (47 g; 0.294 moles) was added in 45 minutes to a suspension of 2-ethyl-2-(6-methoxy-2-naphthyl)-4(R),5(R)-dimethoxycarbonyl-1,3-dioxolane (50 g; 0.134 moles) in toluene (112 ml) cooled to $-10°$ C. Then n.butylmercaptan (25.3 g; 0.281 moles) was added to the reaction mixture which was kept under stirring at $-10°$ C. for 2 hours. After 4 hours at $-10°$ C. the reaction mixture was poured into a solution of sodium bicarbonate (8.4 g) in water (100 ml).

After separation of the phases, the organic phase was evaporated to residue under vacuum. A crude product (83 g) was obtained containing a mixture of 2-[1(S)-bromoethyl]-2-(6-methoxy-2-naphthyl)-4(R),5(R)-dimethoxycarbonyl-1,3-dioxolane and its epimer having RRR configuration in a ratio RRS:RRR=90.4:9.6 (yield 75%).

EXAMPLE 4

Bromine (4.9 g; 0.031 moles) was added in 30 minutes to a solution of 2-ethyl-2-(6-methoxy-2-naphthyl)-4(R),5(R)-dimethoxycarbonyl-1,3-dioxolane (5.6 g; 0.013 moles) in methylene chloride (12.6 ml) cooled to −10° C. The mixture was kept under stirring at −10° C. for 2 hours, then t.butylmercaptan (2.0 g; 0.022 moles) was added dropwise in 2.5 hours.

After 12 hours at −10° C. the reaction mixture was poured into water (30 ml), the phases were separated and the organic phase was washed with water (20 ml), dried with sodium sulphate and evaporated to residue under vacuum. A crude product (8.58 g) was obtained containing a mixture (6.4 g) of 2-[1(S)-bromoethyl]-2-(6-methoxy-2-naphthyl)-4(R),5(R)-dimethoxycarbonyl-1,3-dioxolane and its epimer having RRR configuration having a ratio RRS:RRR=90.3:9.7 (yield 94%).

EXAMPLE 5

Bromine (47 g; 0.294 moles) was added in 1 hour to a suspension of 2-ethyl-2-(6-methoxy-2-naphthyl)-4(R),5(R)-dimethoxycarbonyl-1,3-dioxolane (50 g; 0.134 moles) in toluene (170 ml) cooled to −10° C. Then t.butylmercaptan (25.3 g; 0.281 moles) was added to the reaction mixture, which was kept under stirring at −10° C. for 2 hours.

After 15 hours at −10° C. the reaction mixture was poured into water (45 ml), the phases were separated and the toluenic phase was evaporated to residue under vacuum.

To a solution of the residue (85.2 g) in toluene (110 ml) a solution of potassium hydroxide (18.7 g; 0.334 moles) in water (46 ml) was added in 1 hour under stirring at 25° C.

After 2 hours at 25° C. the phases were separated. To the aqueous solution 37% hydrochloric acid was added so as to bring the solution pH up to 6.0±0.1.

The solution thus obtained was then heated to 90° C. for 17 hours during which the solution pH was kept between 5.0 and 5.8 by subsequent additions of a 32% solution of KOH.

The reaction mixture was then heated at 100° C. for further 8 hours by keeping the pH between 5.0 and 5.4.

37% hydrochloric acid was added to the reaction mixture cooled to 20° C. up to pH 3. diethyl ether (300 ml) was then added, it was kept under stirring for 30 minutes, the suspension was filtered on a porous septum. The mother liquors from filtration were separated and the organic phase was evaporated to residue under vacuum. A crude product (28.9 g) was obtained containing a mixture of S(+)-2-(6-methoxy-2-naphthyl)-propionic acid and its enantiomer R(−) (HPLC titre 80.7%, enantiomeric ratio S:R=95.5, yield 75.7%).

What we claim is:

1. A process for the selective dehalogenation in position 5 of the naphthalenic nucleus of compounds of formula II

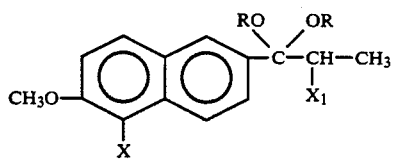
(II)

wherein X and $X_1$, which are the same or different, represent a bromine or chlorine atom; the two R radicals independently represent an alkyl, phenyl or benzyl group, otherwise the two R radicals together represent either a $C_2$-$C_5$ alkylene chain that forms, together with the two oxygen atoms and the carbon to which they are linked, an unsubstituted or alkyl-substituted cyclic structure or the two R radicals together represent a group of the formula

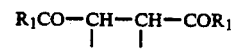

in which the two $R_1$ radicals, which are the same or different, represent an alkoxy, hydroxy or aminic group which process comprises treating a compound of formula II with a dehalogenating agent selected from the group consisting of hydrogen sulfide, aliphatic thiols and mixtures thereof in an inert anhydrous solvent at acidic pH, and the ratio of dehalogenating agent to compound of formula II ranges from 1:1 to 3:1.

2. A process according to claim 1, in which the dehalogenating agent is selected from the group consisting of hydrogen sulfide, methylmercaptan, ethylmercaptan, n-propylmercaptan, n-butylmercaptan, t-butylmercaptan, thioglycolic acid, 1,2-ethanedithiol and mixtures thereof.

3. A process according to claim 1, in which the dehalogenating agent is t-butylmercaptan.

4. A process for the preparation of compounds of formula III

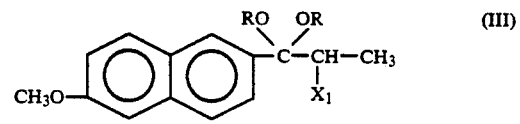
(III)

wherein $X_1$ represents a bromine atom and the two R radicals independently represent an alkyl, phenyl or benzyl group, otherwise the two R radicals together represent either a $C_2$-$C_5$ alkylene chain that forms, together with the two oxygen atoms and the carbon to which they are linked, an unsubstituted or alkyl-substituted cyclic structure or the two R radicals together represent a group of the formula

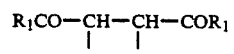

in which the two $R_1$ radicals, which are the same or different, represent an alkoxy, hydroxy or aminic group which process consists of brominating in an organic solvent a compound of formula I

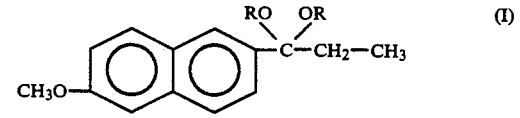
(I)

where the two R radicals are defined above in order to obtain a compound of formula II

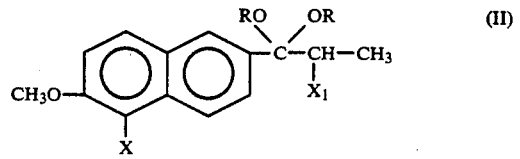
(II)

where X and $X_1$ represent a bromine atom and the two R radicals are as defined above; and selectively debrominating compounds of formula II in the same bromination reaction environment used to produce compounds of formula II by treatment with a dehalogenating agent selected from the group consisting of hydrogen sulfide, methylmercaptan, ethylmercaptan, n-propylmercaptan, n-butylmercaptan, t-butylmercaptan, thioglycolic acid, 1,2-ethanedithiol and mixtures thereof, at a temperature between −20° C. and 20° C., and the ratio of dehalogenating agent to compound of formula II ranges from 1:1 to 3:1.

5. A process according to claim 4 in which the bromination is carried out with bromine in an organic solvent selected from the group consisting of benzene, toluene, nitrobenzene, chlorinated solvents and mixtures thereof.

6. A process according to claim 4 in which the dehalogenating agent is t-butylmercaptan.

7. The process according to claim 1, wherein the process is performed at a temperature of from −20° C. to 20° C.

* * * * *